(12) United States Patent
Häupl et al.

(10) Patent No.: US 7,839,976 B2
(45) Date of Patent: Nov. 23, 2010

(54) X-RAY DEVICE

(75) Inventors: Rainer Häupl, Krummennaab (DE);
Claus-Günter Schliermann, Kemnath (DE); Thomas Will, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 27 days.

(21) Appl. No.: 12/299,073

(22) PCT Filed: May 10, 2007

(86) PCT No.: PCT/EP2007/054538

§ 371 (c)(1),
(2), (4) Date: Oct. 30, 2008

(87) PCT Pub. No.: WO2007/131939

PCT Pub. Date: Nov. 22, 2007

(65) Prior Publication Data

US 2009/0074144 A1 Mar. 19, 2009

(30) Foreign Application Priority Data

May 16, 2006 (DE) .................. 10 2006 022 832

(51) Int. Cl.
*H05G 1/10* (2006.01)
(52) U.S. Cl. ....................... 378/102; 378/197
(58) Field of Classification Search .................. 378/101, 378/102, 194, 197
See application file for complete search history.

(56) References Cited

U.S. PATENT DOCUMENTS 5,410,584 A * 4/1995 Schaefer et al. ............. 378/196
2004/0264642 A1 12/2004 Katcha et al.

FOREIGN PATENT DOCUMENTS

| DE | 74 27 055 | 2/1976 |
|---|---|---|
| DE | 101 42 441 C1 | 3/2003 |
| DE | 10 2004 029 962 A1 | 1/2005 |
| FR | 2 281 697 | 3/1976 |

OTHER PUBLICATIONS

PCT Written Report and International Search Report for PCT/EP2007/054538 dated Jul. 27, 2007 with English translation.
German Office Action dated Apr. 8, 2008 with English translation.
German Office Action dated Jul. 2, 2009 with English translation.

* cited by examiner

*Primary Examiner*—Jurie Yun
(74) *Attorney, Agent, or Firm*—Brinks Hofer Gilson & Lione

(57) ABSTRACT

The X-ray device comprises an X-ray source and a high-voltage generator for supplying the X-ray source with voltage, wherein the high-voltage generator has an intermediate circuit voltage generator and a high-voltage generator, the high-voltage generator is connected to the X-ray source, and the intermediate circuit voltage generator is connected to the high-voltage generator, wherein the intermediate circuit voltage generator and the high-voltage generator are structurally separate and the high-voltage generator is structurally positioned near the X-ray source, thereby keeping the high-voltage line to the X-ray source short.

14 Claims, 4 Drawing Sheets

X-RAY DEVICE

This patent document claims the benefit of PCT/EP 2007/054538 filed on May 10, 2007, which is hereby incorporated by reference. This patent document also claims the benefit of DE 10 2006 022 832.4 filed May 16, 2006, which is also hereby incorporated by reference.

BACKGROUND

The present embodiments relate to an x-ray device with an x-ray source affixed to a gantry.

An x-ray device may have an x-ray source affixed to a ceiling gantry. A high-voltage generating unit for generating high voltage is positioned or fitted on the floor of a room accommodating the x-ray device. The x-ray source is affixed to the end of the ceiling gantry. The ceiling gantry is held in a movable manner in a rail fitted to the ceiling of the room. The x-ray source is connected to the high-voltage generating unit by a high-voltage cable up to 35 m long. The high-voltage cable is affixed to the ceiling by a number of securing devices guided in a displaceable manner on the ceiling. The high-voltage cable hangs down in loops between the securing devices. When the position of the x-ray source changes, the high-voltage cable can be pulled along behind, thus ensuring adequate freedom of movement of the x-ray tube.

Such a conventional x-ray device is disadvantageous in many respects. For example the high-voltage cable, loops of which hand down from the ceiling, impedes the positioning of the x-ray source. Also careless movement of the x-ray tube can cause injury to patients or staff. Provision of the relatively stiff high-voltage cable may require a relatively high expenditure of force to move the x-ray source. Fitting the high-voltage cable is a complex and expensive operation. The conventional relatively long high-voltage cable has a non-negligible capacity, which allows current to flow, with the result that x-ray radiation is still generated, even after the high-voltage generating unit has been disconnected. This in turn increases the applied dose.

Faster disconnection of the x-ray source can be achieved by a grid-controlled x-ray tube. The grid-controlled x-ray tube has complex technology and is very expensive. Alternatively, a single tank x-ray tube, such as an x-ray tube and a high-voltage generating unit in a common housing, may be used. Since the x-ray tube is fitted on a ceiling gantry in a movable manner, if the weight of the x-ray tube is to be kept reasonable and the conditions for its operation are to be acceptable, it is only possible to achieve low levels of power with respect of the x-ray radiation generated. The greater weight of an embodiment with higher power prevents the ceiling gantry from being moved while holding the x-ray tube or requires expending considerable force.

With such x-ray devices with a ceiling gantry the applied dose for an object is controlled by an automatic exposure meter. This automatic exposure meter is set up to predetermine a high tube current and to terminate this during exposure of the object. It is possible to modify the automatic exposure meter to the effect that the exposure process is started with a lower tube current. But the quality of image information generated by the x-ray radiation is more dependent on the thickness of the irradiated object, so the risk of an unclear image increases or the x-ray current has to be tailored in a complex manner to the thickness of the object to be examined.

SUMMARY AND DESCRIPTION

The present embodiments may obviate one or more of the drawbacks or limitations inherent in the related art. For example, in one embodiment, an x-ray device has a simple structure and a short high-voltage line.

In one embodiment, the high-voltage generating unit includes an intermediate circuit voltage generator and a high-voltage generator. The intermediate circuit voltage generator transforms the AC voltage of a supply network serving as the electrical energy supply into an intermediate circuit voltage with a scarcely higher amplitude value and a significantly higher AC voltage frequency. The intermediate circuit voltage supplies the high-voltage generator with electrical energy. The high-voltage generator generates a DC voltage with a high amplitude for the voltage supply to the x-ray tube. The high-voltage generator is connected to the x-ray source by a high-voltage cable.

In one embodiment, the intermediate circuit voltage generator and high-voltage generator may form a unit at a common site. Alternatively, intermediate circuit voltage generator and high-voltage generator may not form a unit at a common site. For example, the intermediate circuit voltage generator may be structurally separate from the high-voltage generator.

The structural arrangement of the high-voltage generator in proximity to the x-ray source allows the length of the cable connecting the high-voltage generator and the x-ray source to be short compared with a conventional x-ray device, so that a quicker disconnection process is possible for the x-ray source. Accordingly, a particularly precise dose may be applied with the proposed x-ray device.

The high-voltage generator may include a device for suspended securing to a ceiling. Accordingly, the high-voltage generator may be fitted to the ceiling in proximity to the x-ray source. The length of the cable connecting the high-voltage generator and the x-ray source can be short. Further structural modifications to the ceiling gantry are not necessary, so this is a particularly economical solution.

In one embodiment, the device for suspended securing is affixed to a housing holding the high-voltage generator. This ensures simple fitting, since the high-voltage generator can be inserted or introduced easily into the housing for fitting purposes.

In one embodiment, the housing is part of the ceiling gantry. This embodiment is compact in structure. This allows the fitting of the x-ray device to be simplified. For example, the high-voltage generator does not have to be separately affixed to the ceiling. Only the supply voltage for the high-voltage generator has to be supplied. The length of the high-voltage conductors for supplying the x-ray source may be short, as only the distance from the high-voltage generator to the x-ray source has to be covered. The high-voltage conductors may run inside the ceiling gantry and only have a maximum length of up to 6 m. Since only the high-voltage generator and not the entire high-voltage generating unit is arranged in the ceiling gantry, the increase in the weight of the ceiling gantry is comparatively small, so that easy operation of the ceiling gantry is ensured.

In one embodiment, the high-voltage generator is affixed to the ceiling in a fixed position and the rail extends from the housing. In this instance a ceiling gantry with almost no modifications compared with the prior art can be used. The ceiling gantry is relatively light and can therefore be displaced easily.

In one embodiment, at least one conductor rail is provided on the rail and at least one sliding contact that interacts with the conductor rail is provided on the ceiling gantry, to produce a voltage supply for the x-ray source. The sliding conduct interacts with the conductor rail, such that there is no need for the conventionally long high-voltage cable connecting the high-voltage generator to the x-ray tube. There is no need for the expenditure of force caused by the dragging along behind of the high-voltage cable when moving the x-ray tube. The x-ray source held on the ceiling gantry in a movable manner can be moved easily so that additional motor facilities for moving the x-ray source can be and are dispensed with. The risk of injury due to the dragging along behind of a high-voltage cable is avoided. To ensure adequate freedom of movement of the x-ray tube, the length of the conductor rail is significantly shorter than the conventional high-voltage cable. It is therefore possible to apply a required dose precisely. The arrangement of a conductor rail interacting with the sliding contact simplified fitting of the x-ray device.

The proposed combination of a conductor rail and a sliding contact is expediently embodied so that it can be used to supply the x-ray tube with currents in the low, medium and high-voltage ranges.

If the high-voltage generator is arranged in the ceiling gantry, the conductor rail may represents the connection between the intermediate voltage circuit and the high-voltage circuit. Accordingly, the conductor rail and sliding contacts may be embodied simply. A length of a high-voltage connection from the high-voltage generator to the x-ray source may be short, thereby minimizing capacitive effects.

DETAILED DESCRIPTION

Figure 1:
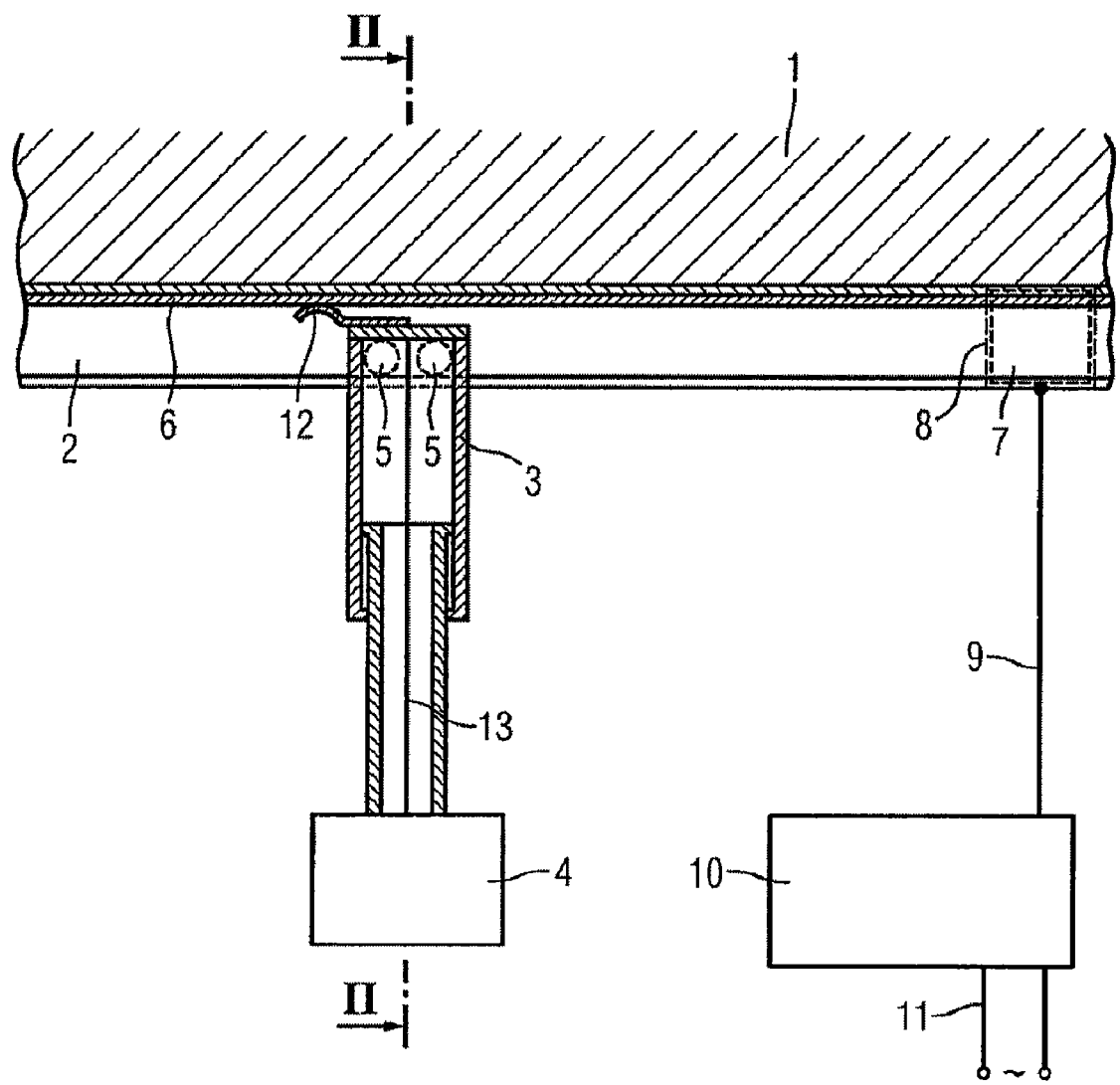
FIG. 1 shows a first embodiment of an x-ray device.
Figure 2:
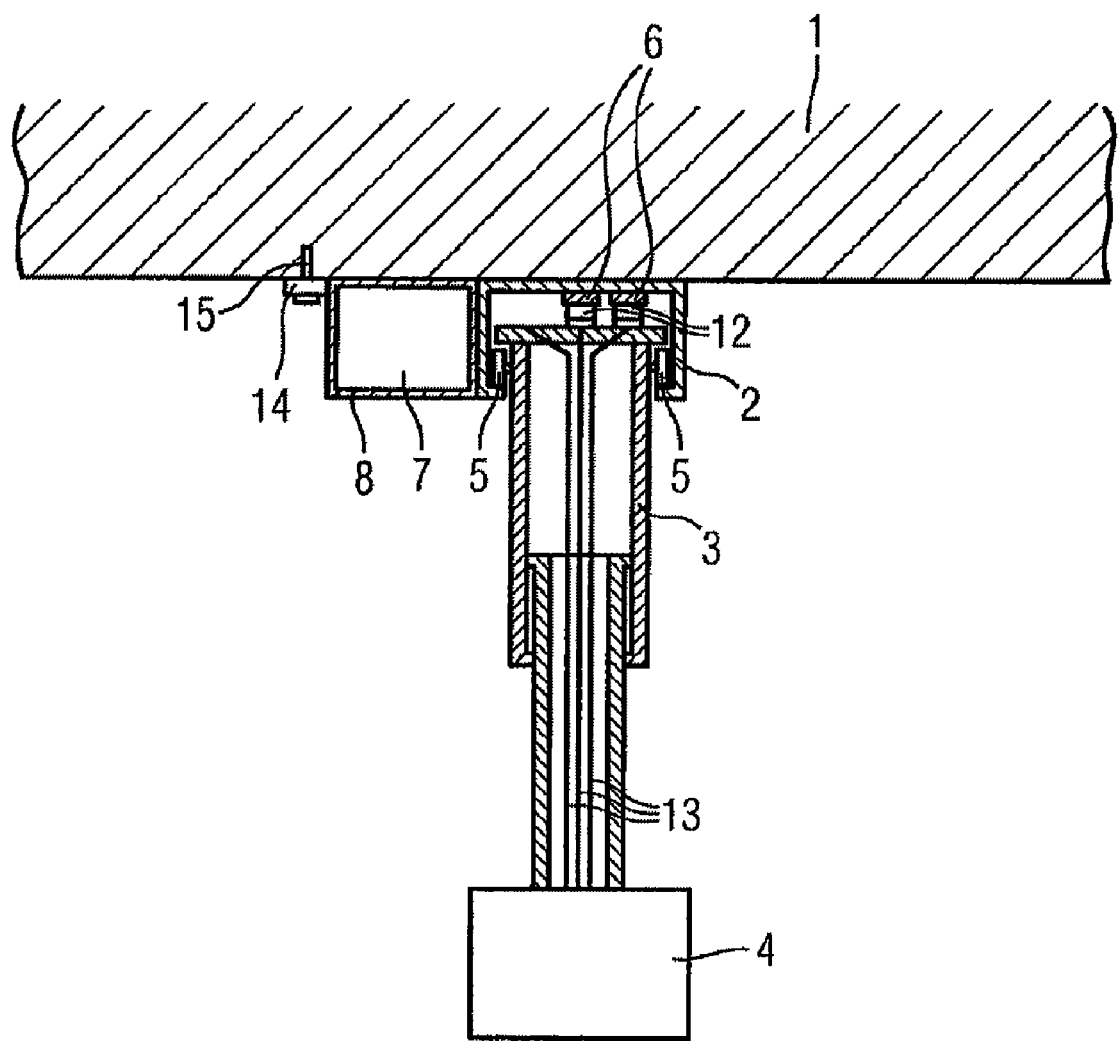
FIG. 2 shows the embodiment according to FIG. 1 along the sectional plane II-II perpendicular to FIG. 1 in FIG. 1.

FIG. 1 and FIG. 2 show an x-ray device. A rail 2 is affixed to a ceiling 1, along which a ceiling gantry 3, which may be telescopic, can be moved. An x-ray source 4 is affixed to the end of the ceiling gantry 3. The rail 2 is configured in the manner of a U-profile. Further U-profiles point inward and are affixed to the two arms of the U-profile. The further U-profiles serve as guide rails for rollers 5 affixed to the ceiling gantry 3. Two conductor rails 6 are affixed to a base plate of the U-profile between the arms of the rail 3. An electrically insulating layer may be disposed in between. The conductor rails 6 are connected in an electrically conducting manner to a high-voltage generator 7. The high-voltage generator 7 is accommodated in a housing 8. It is connected by way of a low-voltage cable 9 to an intermediate circuit voltage generator 10 for a voltage supply. The intermediate circuit voltage generator 10 is supplied with voltage by a main connection 11.

The high-voltage generator 7 and the intermediate circuit voltage generator 10 form the high-voltage generating unit. The intermediate circuit voltage generator 10 can be located a long distance locationally from the high-voltage generator 7, for example, in a different room, because of the low capacity of the low-voltage cable 9 connecting the high-voltage generator 7 to the intermediate circuit voltage generator 10.

High voltage is present at the conductor rails 6 connecting the high-voltage generator 7 and the ceiling gantry 3. Sliding contacts 12, which correspond to the conductor rails 6, are provided on the ceiling gantry 3, being pressed against the conductor rails 6 by spring loading. The sliding contacts 12 are connected to the x-ray source 4 in an electrically conducting manner by a high-voltage cable 13.

As shown in FIG. 2, the housing 8 enclosing the high-voltage generator 7 is provided with a tab 14 projecting from it at an angle, through which a screw 15 is passed to secure the housing 8 to the ceiling 1. The housing 8 is fitted in proximity to the ceiling gantry 3, so that the distance covered by the power rails 6 is short. On the opposite side, the housing of the high-voltage generator 7 can be secured to the rail 2, for example, by screws or by suspension. The high-voltage generator 7 may be secured to the ceiling 1 in a different manner. A fitting plate can be affixed to the ceiling 1, having projections, recesses or rails, to interact with the high-voltage generator 7 in such a manner that the high-voltage generator 7 is suspended from the fitting plate or can be inserted into the fitting plate.

The housing 8 may include the high-voltage generator 7 in proximity to the x-ray source 4. High voltage is only present at the high-voltage conductor between the high-voltage generator 8 and the x-ray source 4, which is embodied as a conductor rail 6 and high-voltage cable 13. Accordingly, the capacity of the high-voltage conductor is kept low. The x-ray source 4 can be disconnected quickly.

Figure 3:
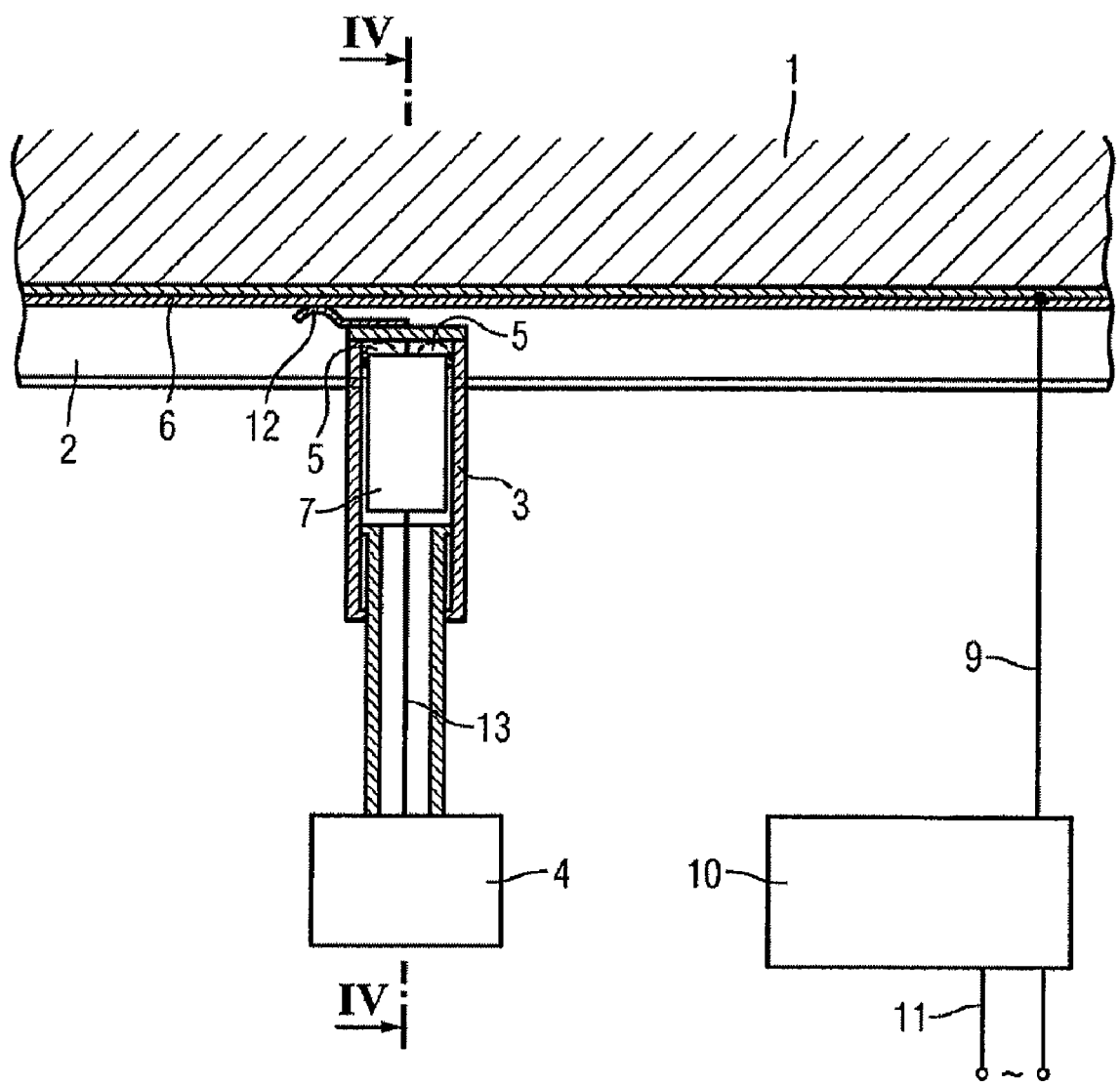
FIG. 3 shows a second embodiment of the x-ray device.
Figure 4:
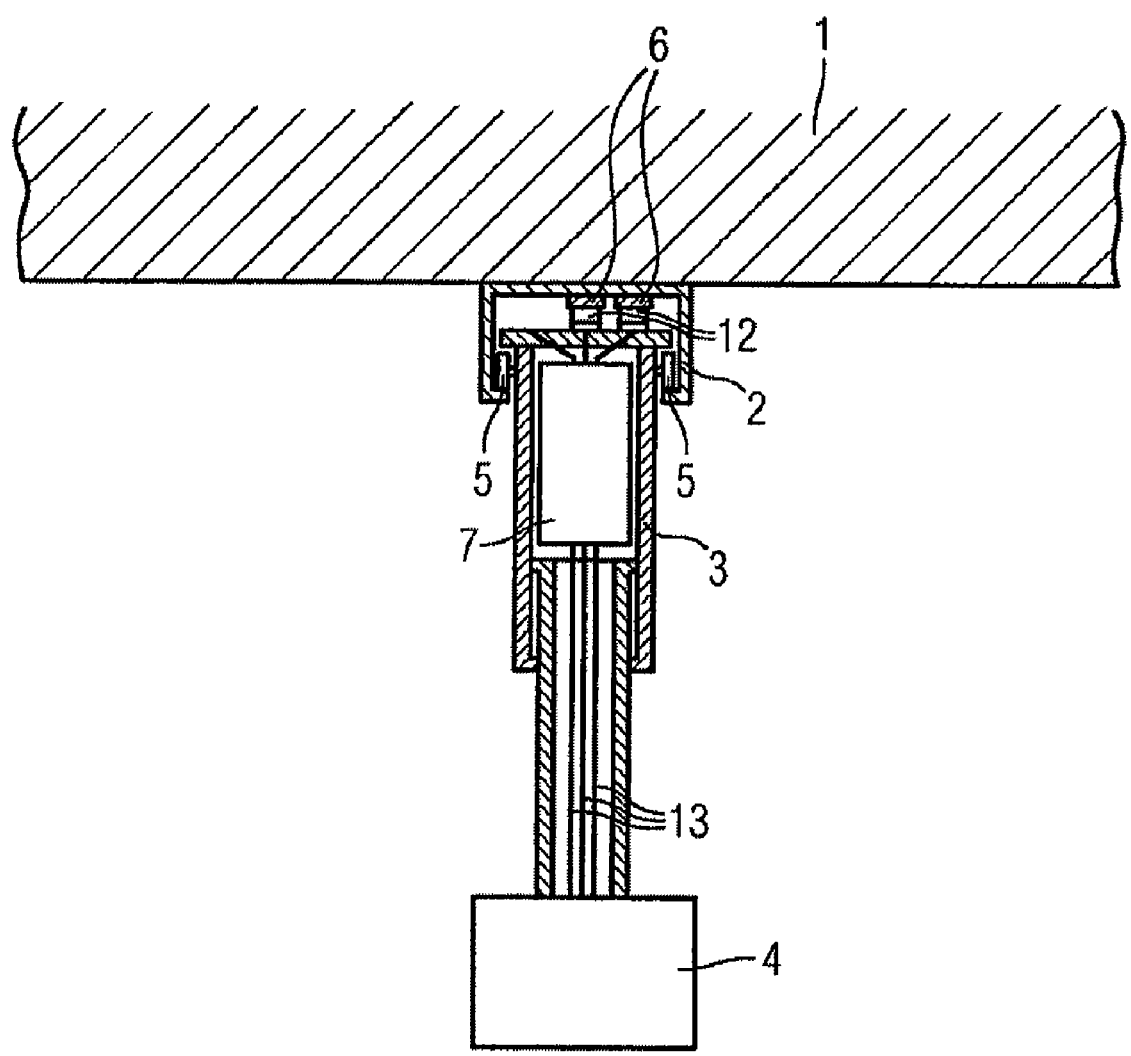
FIG. 4 shows the embodiment according to FIG. 3 along the sectional plane IV-IV perpendicular to FIG. 3 in FIG. 3.

FIGS. 3 and 4 show a second embodiment of the x-ray device. Here the high-voltage generator 7 is accommodated in the ceiling gantry 3. The ceiling gantry 3 has appropriately embodied gantry housing for this purpose in proximity to the rail 2. The gantry housing may include the high-voltage generator 7. Since the high-voltage generator 7 is of comparatively small structure, it can be integrated easily in the ceiling gantry 3. Easy operation of the ceiling gantry 3 remains ensured. The high-voltage generator 7 is supplied with a supply voltage required to operate the high-voltage generator 7 by way of the conductor rails 6. The conductor rails 6 are supplied directly with voltage from the intermediate circuit voltage generator 10 by way of the low-voltage cable 9.

The high-voltage conductor is restricted to the high-voltage cable 13, which connects the high-voltage generator 7 to the x-ray source 4. The capacity of the high-voltage conductor is further reduced here compared with the variant shown in FIGS. 1 and 2. The x-ray source 4 can be disconnected particularly quickly.

The rollers 5, which support the ceiling gantry 3 together with the high-voltage generator 7 and are guided in the rail 2, secure the high-voltage generator 7 to the ceiling 1.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. An x-ray device comprising:

a gantry;

an x-ray source affixed to the gantry and a high-voltage generating unit that is operable to supply the x-ray source with voltage, the high-voltage generating unit having an intermediate circuit voltage generator and a high-voltage generator; and a securing device that is operable to secure the high-voltage generator to a ceiling, wherein the high-voltage generator is connected to the x-ray source and the intermediate circuit voltage generator is connected to the high-voltage generator, the intermediate circuit voltage generator and the high-voltage generator being structurally separate and the high-voltage generator being arranged structurally in proximity to the x-ray source, and wherein the gantry is a ceiling gantry.

2. The x-ray device as claimed in claim 1, wherein the securing device is affixed to a housing of the high-voltage generator.

3. The x-ray device as claimed in claim 2, wherein the gantry includes the high-voltage generator.

4. The x-ray device as claimed in claim 2, wherein the gantry is displaceable along a rail affixed to the ceiling.

5. The x-ray device as claimed in claim 4, wherein the high-voltage generator is affixed to the ceiling in a fixed position and the rail extends out from the high-voltage generator.

6. The x-ray device as claimed in claim 5, wherein at least one conductor rail is provided on the rail and at least one sliding contact, which interacts with the conductor rail, is provided on the gantry to supply voltage to the x-ray source.

7. The x-ray device as claimed in claim 4, wherein the securing device includes the rail affixed to the ceiling, such that the gantry can be moved along the rail.

8. The x-ray device as claimed in claim 1, wherein the ceiling gantry includes the high-voltage generator.

9. The x-ray device as claimed in claim 8, wherein the ceiling gantry is displaceable along a rail affixed to the ceiling.

10. The x-ray device as claimed in claim 1, wherein the high-voltage generator is affixed to the ceiling in a fixed position and a rail extends out from the high-voltage generator.

11. The x-ray device as claimed in claim 10, wherein at least one conductor rail is provided on the rail and at least one sliding contact, which interacts with the conductor rail, is provided on the ceiling gantry to supply voltage to the x-ray source.

12. The x-ray device as claimed in claim 1, wherein the securing device includes a rail affixed to the ceiling, such that the ceiling gantry is moved along the rail.

13. The x-ray device as claimed in claim 12, wherein the x-ray source is affixed to an end of the ceiling gantry and the ceiling gantry is telescopic.

14. The x-ray device as claimed in claim 13, wherein the rail includes a U-profile.

* * * * *